United States Patent
Suh et al.

(10) Patent No.: US 9,162,899 B2
(45) Date of Patent: Oct. 20, 2015

(54) BAX TYPE ZEOLITE GRANULE AND PROCESS FOR PREPARING THE SAME

(75) Inventors: Jeong Kwon Suh, Daejeon (KR); Beom Sik Kim, Daejeon (KR); Yun Ho Jeong, Daejeon (KR); Jin Suk Lee, Seoul (KR); Won Young Kim, Daejeon (KR); Ho Sik Chang, Daejeon (KR)

(73) Assignee: SAMSUNG TOTAL PETROCHEMICALS CO., LTD., Seosan-Si (KR)

( * ) Notice: Subject to any disclaimer, the term of this patent is extended or adjusted under 35 U.S.C. 154(b) by 550 days.

(21) Appl. No.: 13/541,395

(22) Filed: Jul. 3, 2012

(65) Prior Publication Data

US 2013/0012377 A1 Jan. 10, 2013

(30) Foreign Application Priority Data

Jul. 5, 2011 (KR) .................. 10-2011-0066308

(51) Int. Cl.
| | | |
|---|---|---|
| *B01J 20/18* | (2006.01) | |
| *C01B 39/48* | (2006.01) | |
| *B01J 20/30* | (2006.01) | |
| *C07C 7/13* | (2006.01) | |
| *B01J 20/28* | (2006.01) | |

(52) U.S. Cl.
CPC ............. *C01B 39/48* (2013.01); *B01J 20/18* (2013.01); *B01J 20/183* (2013.01); *B01J 20/186* (2013.01); *B01J 20/2803* (2013.01); *B01J 20/28004* (2013.01); *B01J 20/305* (2013.01); *B01J 20/3007* (2013.01); *B01J 20/3028* (2013.01); *B01J 20/3042* (2013.01); *B01J 20/3078* (2013.01); *B01J 20/3085* (2013.01); *C07C 7/13* (2013.01); *C07C 2529/08* (2013.01)

(58) Field of Classification Search
USPC ............. 502/60, 62, 63, 64, 67, 79, 400, 407, 502/411, 414
See application file for complete search history.

(56) References Cited

U.S. PATENT DOCUMENTS

| | | | |
|---|---|---|---|
| 4,603,040 A | 7/1986 | Kuznicki et al. | |
| 5,001,098 A | 3/1991 | Pacaud et al. | |
| 5,132,260 A * | 7/1992 | Plee ............................. | 502/64 |
| 5,292,360 A | 3/1994 | Pacaud et al. | |
| 6,030,916 A * | 2/2000 | Choudary et al. ............ | 502/65 |
| 6,425,940 B1 * | 7/2002 | Chao et al. ................... | 95/130 |
| 6,458,736 B2 * | 10/2002 | Mohr et al. ................... | 502/67 |
| 6,743,745 B2 | 6/2004 | Jaussaud et al. | |
| 7,732,372 B2 * | 6/2010 | Hampden-Smith et al. .. | 502/407 |
| 2001/0049998 A1 * | 12/2001 | Rode et al. ................... | 95/117 |
| 2008/0274345 A1 * | 11/2008 | Fuesting et al. ............ | 428/306.6 |
| 2009/0326308 A1 * | 12/2009 | Kulprathipanja et al. ..... | 585/820 |
| 2011/0104494 A1 * | 5/2011 | Brandt et al. ................ | 428/402 |
| 2011/0105301 A1 * | 5/2011 | Wang et al. ................... | 502/62 |
| 2012/0247334 A1 * | 10/2012 | Hurst et al. ................... | 95/147 |
| 2012/0264992 A1 * | 10/2012 | Hurst et al. ................... | 585/824 |

OTHER PUBLICATIONS

English translation of CN 1358566, Jul. 2002.*

* cited by examiner

*Primary Examiner* — Elizabeth Wood
(74) *Attorney, Agent, or Firm* — Harness, Dickey & Pierce, P.L.C.

(57) ABSTRACT

The present invention provides a method for preparing a BaX type zeolite granules comprising: adding a carbohydrate-based molding promoter to NaX type zeolite powder and thereto subsequently spraying and blending alumina sol and silica sol to form granules of the mixture; heating the formed granules to convert the alumina and silica component to aluminosilica so as to generate pores inside the formed granules; hydrothermally treating the resulted granules in a sodium hydroxide aqueous solution under the conditions for zeolite synthesis, thereby converting a portion of the aluminosilica to zeolite; and carrying out ion-exchanging by Ba ions. The present invention also provides BaX type zeolite granules which have excellent strength and can be suitably used as an adsorbent in simulated moving bed (SMB) application.

9 Claims, No Drawings

BAX TYPE ZEOLITE GRANULE AND PROCESS FOR PREPARING THE SAME

CROSS-REFERENCE TO RELATED APPLICATION

This application claims the benefit of Korean Patent Application No. 10-2011-0066308 filed on Jul. 5, 2011, the entire disclosure of which is incorporated herein by reference.

TECHNICAL FIELD OF THE INVENTION

The present invention provides BaX type Zeolite granules having excellent strength and para-xylene adsorption and a method for preparing the same. Specifically, the present invention provide a method for preparing a BaX type zeolite comprising the steps of: adding a carbohydrate-based molding promoter to NaX type zeolite powder and thereto subsequently spraying and blending alumina sol and silica sol to form granules of the mixture; heating the formed granules to convert alumina and silica components to aluminosilica so as to generate pores inside the formed granules; hydrothermally treating the resulted granules in a sodium hydroxide aqueous solution under the conditions for zeolite synthesis, thereby converting a portion of the aluminosilica, i.e. the binding agent component inside the formed granules, to zeolite; and carrying out ion-exchanging by Ba ions. Thus obtained BaX type zeolite has excellent strength and can be suitably used as an adsorbent in simulated moving bed (SMB) application.

BACKGROUND OF THE INVENTION

As for technologies for separation of materials which can be hardly separated by a generally used distillation process, it is known that various technologies such as adsorption, extraction, crystallization, membrane separation and the like can be used.

Para-xylene is a very important basic material in an industrial point. Separation of para-xylene used to be carried out by a crystallization process for some while and in recent years a SMB process, an energy-saving process has been being dominantly used. An adsorbent applicable to such SMB process should have excellent selective adsorption properties to a desired substance and be in the form of granules having high strength so as to be resistant to high temperature and high pressure. So far well-known adsorbent applicable to an SMB process for para-xylene separation is zeolite, which is mainly used in this field of art and particularly, a BaX type zeolite is most preferably used.

Zeolite is an crystalline aluminosillicate represented by the following formula 1:

$$M_{x/n}[(AlO_2)_x(SiO_2)_y]\cdot wH_2O \qquad \text{[Formula 1]}$$

wherein, M is a cataion; n is an atomic valence; w is a molecular number of water of crystallization; x and y are integers varied depending on the crystalline structure.

Generally, zeolite has micropores having a diameter of 3-10 Å, having a molecular sieving effect, and owing to such structure, it further has a unique property of selectively adsorbing a certain molecules. Particularly, as a hydrophilic adsorbent, it shows strong adsorption to polar molecules such as water even under low partial pressure and high temperature conditions. In the meantime, although zeolite has a selective adsorption property as described above, its fine powdery form with the average particle size of several μm caused many inconveniences in practical use in adsorption or catalytic process.

Therefore, for the use of zeolite as a suitable adsorbent in practical industrial processes such as SMB process, it should undergo a molding process into a certain form with the addition of a binder.

As for so-far known conventional methods for the molding method of zeolite, for example, widely used is a method comprising the steps of: ion-exchanging zeolite utilizing a suitable cation and drying; adding a binder at the amount of about 30 wt % or less per particle for granulation and molding; subsequently calcinating the resulted product at 600-800° C.

As for the specific example of above-described conventional methods, a method for preparing an adsorbent by converting 4A type zeolite to 5A type zeolite via replacement of sodium ions in 4A type zeolite by calcium ions, then extruding and molding the converted 5A type zeolite using a natural clay of the kaolinite family as an inorganic binder, and calcinating the resultant. (see, U.S. Pat. Nos. 5,001,098 and 5,292,360, etc.). However, the above-mentioned method requires complicated filtering and washing process disadvantageously, since zeolite particles having several to several tens of μm size generated after the ion-exchange are present in a slurry phase. Moreover, the natural clay used as a binder for increasing the mechanical strength remains in the final product, thereby deteriorating the adsorption property.

In order to overcome such problems mentioned above, U.S. Pat. No. 6,743,745 discloses a method for preparing a zeolite granule in which the binder content can be minimized by blending approximately 2-15 wt % of highly dispersed attapulgite. From the above method, obtained is a zeolite granule in which about 10 wt % of the highly dispersed attapulgite remains inactive, and the remained highly dispersed attapulgite encompasses the zeolite component. Owing to such structures, it also has another disadvantage such that the diffusion of a gas component to be separated through the inside or outside of the granule is hindered, and thus the adsorption-desorption rate which is one of the important factors in SMB process is limited.

U.S. Pat. No. 4,603,040 discloses a method for a zeolite granule having improved adsorption property by forming a zeolite preform by using a kaolin binder, heating the zeolite preform at or above 600° C., placing the heated product in an aqueous alkaline solution for a long period of time such as 10 or more days so as to convert the binder component to zeolite. However, said method takes so long time to complete the process, it is deemed not to be industrially available in practical point of view.

For improving such method, for example, Korean Patent No. 10-0538961 discloses a method for preparing a low-content silica X type granular aggregates having inert binder at a low content, by blending it with about 15 wt % of natural clay (kaolin or montmorillonite type), calcinating the mixture at about 600° C., treating it with a mixed aqueous solution of sodium hydroxide and potassium hydroxide for at most 24 hours. However, said method also has disadvantages that, owing to the use of natural clay as a binder which causes shrinks during the calcinating process, the mechanical strength of the zeolite granule becomes decreased, thereby generating a great amount of dust, clogging most of the pores and thus making material transmission difficult.

In the meantime, DE patent No. 1,165,562 describes a method for preparing a binderless or binder-free zeolite by forming zeolite by using a silica sol as a binder and converting the silica component to zeolite by an aqueous solution of sodium aluminate. However, said method is reported to have defects such that the silica component served as a binder is exuded into the reaction mother liquor during said process and thus significantly decreases the strength of the final product.

As a method to overcome the problem of said DE patent, JP laid-open patent publication No. Heisei 6-53569 describes improvement in strength of a zeolite containing said silica binder by treating it with an alkali earth metal salt. According to said method, the zeolite component only inside the formed body can be converted to the zeolite in the form of alkali metal ion by ion exchange, and salts are penetrated and settled down in the voids formed between the silica component and the zeolite crystal particles, resulting in improvement in strength. However, material diffusion through the inside of the voids is inhibited, and thus the adsorption property is deteriorated.

Further, JP patent No. 4188050 describes a method for preparing a microspheric zeolite utilizing alumina sol. However, said method utilizes the alumina sol only as a binder and said alumina component remains as it is inside the resulted product, thereby lowering the adsorption property. Further, said method involves a complex process which comprises a first assembly process of a slurry mixture via a spray-drying process and then a second molding process for forming pellets.

As described above, the conventional adsorbents applied to a SMB process is prepared by blending a clay-type inorganic binder with a zeolite powder, molding and calcinating, or by treating a calcinated zeolite granules with an aqueous alkaline solution to convert a clay-type inorganic binder component into zeolite. However, these adsorbents prepared by such methods have problems such that impurities present in such clay-type inorganic binder still remain in the resulted granules and thus the improvement of adsorptive separation capability and mechanical strength is limited.

SUMMARY OF THE INVENTION

The object of the present invention is to overcome the problems of prior arts and to provide a BaX type zeolite granule which has pores formed well inside the granule, excellent adsorptive separation property selective to para-xylene, high bulk density and excellent mechanical strength, thereby being suitably used as an adsorbent in a SMB process for para-xylene adsorptive separation operated under high temperature and pressure conditions so as to produce high-purity para-xylene, through a simplified process, while minimizing a binder content.

Further object of the present invention is to provide a method for preparing the BaX type zeolite granules.

DETAILED DESCRIPTION OF THE INVENTION

The present inventors have attempted to solve the above-mentioned problems of the prior arts, and finally achieved a zeolite in a granular form by a method comprising the following steps: adding a carbohydrate-based molding promoter to NaX type zeolite powder and subsequently blending alumina sol and silica sol as an inorganic binder; classifying; drying; heat-treating in the air so as to remove the carbohydrate-based molding promoter; and converting the alumina sol and silica sol served as a binder, into amorphous aluminosilica by regulating moisture and water of crystallization, thereby forming the pores, wherein thus formed pores facilitate permeation of an aqueous alkaline solution into the inside of the granular zeolite during the hydrothermal treatment; treating thus obtained granular zeolite having a certain range of particle size by an aqueous solution of sodium hydroxide to directly convert the inorganic binder component, i.e. aluminosilica to zeolite to the desired ratio; and then thus obtained zeolite is ion-exchanged by barium ions so as to minimize the binder component, resulting in a novel BaX type granular zeolite which has pores uniformly well-formed even inside thereof, thus has excellent adsorptive separation property, high bulk density, superior mechanical strength.

Specifically, the method for preparing a BaX type granular zeolite according to the present invention is characterized by comprising the following steps:

(1) adding a carbohydrate-based molding promoter to NaX type zeolite powder and thereto subsequently spraying and blending alumina sol and silica sol to form granules;

(2) classifying the formed granules, obtaining granules having a size of 0.25-1.20 mm;

(3) drying thus obtained granules and then calcinating the dried granules at the temperature range of 200-500° C. so as to remove the carbohydrate-based molding promoter, and converting the alumina and silica to aluminosilica by regulating the moisture and water of crystallization of the binder component, thereby generating pores;

(4) placing the calcinated granules obtained from above step (3) in an aqueous solution of sodium hydroxide to allow a hydrothermal reaction, and separating and washing the resulted granules from the reaction solution;

(5) treating the granules obtained from the above step (4) with aqueous barium ion solution for ion-exchange, then washing and drying the resultant; and (6) heating the dried granules obtained from the above step (5) at the temperature range of 350-650° C. to remove water of crystallization from the zeolite and activate the resulted product.

In the method for preparing a BaX type zeolite granules according to the present invention, the step (1) is a process for forming zeolite in granular form, in which a NaX type zeolite powder and a carbohydrate-based molding promoter are placed in a molding device, thereto alumina sol and silica sol are subsequently sprayed via a nozzle and blended together, and the blend is granulated to the size ranged between 0.21-3.20 mm.

In the present invention, NaX type zeolite is used as a raw material, which has microvoids inside the catalyst, thereby having a unique effect as a molecular sieve being capable of selectively adsorbing specific molecules. The species of NaX type zeolite are not specifically limited and any NaX type zeolite conventionally used in the art may be used.

The carbohydrate molding promoter used in the above step (1) helps to facilitate aggregation of powdery zeolite into a granular form during the molding process. The carbohydrate molding promoter which can be used in the present invention includes cellulose, lignin, starch or alginic acid, etc., and the suitable blending ratio is 5-25 parts by weight based on 100 parts by weight of zeolite. When the amount is less than 5 parts by weight, irregular granules are formed from the molding process, while the amount is more than 25 parts by weight, the granules absorb a great amount of moisture, decreasing the density of the final product and thus significantly reducing the strength.

The alumina sol used in the step (1), which substantially acts as a binder, is not limited to certain species and those conventionally used in this field of art may be used. The suitable amount of alumina sol used is 10-40 parts by weight based on 100 parts by weight of zeolite. When the amount of alumina sol is less than 10 parts by weight, the binding strength is poor and the bulk density becomes decreased, thereby lowering the strength, while it is more than 40 parts by weight, the bulk density of the resulted granule becomes increased too much so that material transmission into the granule becomes difficult, disadvantageously. As for the alumina sol, an aqueous solution containing 10-20 wt % of an alumina component is preferably used. When the alumina content in the alumina sol is less than 10 wt %, the binding strength is poor and the bulk density becomes decreased, thereby lowering the strength, while it is more than 20 wt %, it is difficult to find a commercially available product, disadvantageously.

The silica sol used in the above step (1) is not specifically limited to certain species, and any silica sol conventionally used in this field of art may be used. The suitable amount of the silica sol used is 20-80 parts by weight based on 100 parts by weight of zeolite. When the amount of silica sol is less than 20 parts by weight, the binding strength is poor and the bulk density becomes decreased, thereby lowering the strength, while it is more than 80 parts by weight, the bulk density of the resulted granule becomes increased too much so that material transmission into the granule becomes difficult, disadvantageously. As for the silica sol, an aqueous solution containing 15-30 wt % of a silica component is preferably used. When the silica content in the silica sol is less than 15 wt %, the binding strength is poor and the bulk density becomes decreased, thereby lowering the strength, while it is more than 30 wt %, it is difficult to find a commercially available product, disadvantageously.

The molding device used in the present invention is not specifically limited as long as it is capable of blending the zeolite material, the carbohydrate-based molding promoter, a blend of alumina sol and silica sol and forming the blend into granules, and any molding device conventionally used in this field of art may be used. For example, those selected from a flowshear mixer, a disc granulator, an extrusion granulator, a fluidized bed granulator and a compressive disintegration granulator.

The step (2) of the present invention is a classification step, wherein the formed granules are classified by a classifier and formed granules having a particle diameter in the range of 0.25-1.20 mm, preferably 0.355-0.850 mm are taken from the classifier, so as to be applied to the following step (3). Those out of the range of 0.25-1.20 mm are not suitable for the application to a conventional SMB process, since it causes problems in said process. Therefore, the formed granules out of said range of 0.25-1.20 mm are separated out, dried, disintegrated, powdered and recycled again to the molding device of the step (1), wherein the recycled powder is mixed together with a freshly fed zeolite powder and used as a core in the process of step (1). The amount of the recycled powder is 20-50 wt % based on the total amount of zeolite powder fed in the step (1), in other words, the freshly fed zeolite powder and the recycled powder are preferably mixed at the ratio of the freshly fed zeolite powder:recycled powder=50-80 wt %:20-50 wt %. When the amount of the recycled powder is out of said range, particle size regulation becomes difficult in a granulation process.

By the classification, disintegration and recycling process according to the present invention, it is possible to relatively easily regulate the size of the formed granule in a granulation process in which particle size regulation is generally known to be complicated, and also possible to provide granules with improved roundness, thereby being capable of reducing the porosity when the formed granules are filled in an adsorption column.

In the step (3) of the present invention, the granules having a particle diameter of 0.25-1.20 mm, preferably 0.355-0.850 mm obtained from said classification process are dried and heat-treated at about 200-500° C. in the air. The dry conditions and method are not specifically limited. According to such dry and heat treatment process, the carbohydrate-based molding promoter is removed, and the alumina component and the silica component is converted to aluminosilica, thereby forming pores, while regulating the residual moisture and water of crystallization bound to the alumina component and silica component. When the heat treatment temperature is less than 200° C., water of crystallization is not smoothly regulated and thus pores are only slightly formed, while it is more than 500° C., phase transition of the aluminosilica component occurs, resulting in decreasing the porosity disadvantageously.

In the step (4) of the present invention, the heat-treated granules hydrothermally react with an aqueous solution of sodium hydroxide to convert a portion of the aluminosilica component contained as a binder to a NaX type zeolite. The composition and concentration of the aqueous reaction solution and conditions for the hydrothermal reaction may be those conventionally used in conventional hydrothermal reactions for converting some amount of the binder, i.e. aluminosilica to zeolite. When treating the granules with an aqueous solution of sodium hydroxide, the reaction conditions may be conventional conditions for hydrothermal reaction, for example preferably aging at about 20-50° C. for about 6-24 hours and hydrothermally reacting at the range of 70-95° C. for 4-24 hours. When the aging temperature is too low as much as less than 20° C., the time for aging should be lengthened, causing decrease in efficiency, while it is too high as much as more than 50° C., it directly undergoes a crystallization process without formation of zeolite seeds and thus the conversion of a binder component to zeolite becomes difficult. When the temperature for the hydrothermal reaction is less than 70° C., the hydrothermal reactions proceed very slow, while it is more than 95° C., crystallization so rapidly occurs and accordingly various types of zeolite generated being admixed, disadvantageously. After suitable aging and hydrothermal reaction as described above, the reaction mother liquor is removed and washed sufficiently.

The following reaction scheme 1 represents the conversion of binder components, i.e. alumina ($Al_2O_3$) and silica ($SiO_2$) to aluminosilica in the heat treatment process; and the reaction scheme 2 represents the chemical reaction that occurs when treating with an aqueous solution of sodium hydroxide to convert to NaX type zeolite.

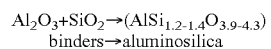
binders→aluminosilica  [Reaction scheme 1]

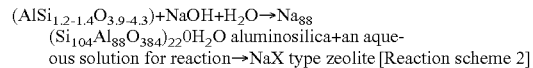
($Si_{104}Al_{88}O_{384}$)$_{22}0H_2O$ aluminosilica+an aqueous solution for reaction→NaX type zeolite [Reaction scheme 2]

According to the reaction scheme 2, some of the aluminosilica which acts as a binder with a few adsorption capability are converted to zeolite, therefore the adsorptive separation capability of the granule becomes improved via said process. In the meantime, reaction mother liquor can be penetrated through pores present inside the granule, before the reaction, and this facilitate the contact between the reaction mother liquor and aluminosilica component. Therefore, generated zeolite remains as it is inside the pores, increasing the bulk density and the strength of the granule.

In the step (5), the hydrothermally reacted granules are contacted with an aqueous solution containing barium ions, so as to ion-exchange the cations ($Na^+$) present within the crystal lattice of zeolite by barium ions ($Ba^{2+}$). As for the aqueous solution of barium ions, any aqueous solution of barium ions may be used, for example, 2N aqueous solution of $BaCl_2$ may be suitably used. The ion-exchange method is preferably carried out by continuously passing the flow of an aqueous solution of barium ions through the granule as a stationary phase. The ion-exchanged granules are sufficiently washed and then dried. The ion exchange ratio by barium ion in the step (5) is preferably 85% or more, in view of the strength and adsorption capability.

Finally, in the step (6) of the present invention, the ion-exchanged granules obtained from the step (5) are placed, for example in a batch type rotary furnace and heat-treated at 350-650° C., preferably 400-550° C. for 0.3-3.0 hour under the sufficient flow of air free of moisture and carbon dioxide, so as to prepare the final product. When the calcinating temperature is less than 350° C., it is difficult to remove water of crystallization, while it is more than 650° C., owing to sintering of the granules, the number of pores becomes decreased and thus adsorption capability is further decreased. As for the furnace which may be used in the step (6), a stationary furnace, a tunnel type furnace, a high frequency heating furnace and Helshof multistage furnace may be used other than the rotary furnace.

The present invention further relates to the BaX type zeolite granules prepared by the method according to the present invention. The BaX type zeolite granules have well-developed micropores, mesopores and macropores, thus excellent selective adsorption capability, particularly to para-xylene, thereby being suitably used as an adsorbent in a device for para-xylene production with high purity.

The BaX type zeolite granule prepared by the method of the present invention contains 90.0 wt % or more of zeolite, 10.0 wt % or less of aluminosilica, on a solid basis; has 0.095 g/g or more of para-xylene adsorption capability under the conditions of 177° C., 8.9 Kg; 0.65 g/ml or more of bulk density (8×12 ASTM Mesh); 97% or more of abrasion resistance (20×25 ASTM Mesh); and 0.102 g/hour or more of para-xylene generation per unit amount (g) of the BaX type granular zeolite from a para-xylene producing device using a SMB process.

Embodiments to Carry Out the Invention

The present invention is further illustrated with a reference to the following examples, however it should be understood that the scope of the invention is not limited by such illustrative examples.

Example

A NaX type zeolite powder (water content 5.40 wt %) 14.0 kg, a cellulose powder 1.5 kg, and a recycled zeolite powder 6.0 kg (average particle size: 31.2 μm; water content: 6.50 wt %) were placed into a 130 l volume flowshear mixer (Germany), and mixed together at the spindle rotational speed of 180 rpm and the chopper rotational speed of 3600 rpm for 1 min.

Next, a solution prepared by blending alumina sol ($Al_2O_3$: 20.0 wt %) 3.82 kg and water 1.62 kg was fed to the above prepared powder mixture via nozzle and kneaded together. Then, while feeding thereto a solution prepared by blending silica sol ($SiO_2$: 30 wt %) 4.53 kg and water 1.95 kg via nozzle, granulation was carried out for 15 minutes to obtain granules having a particle diameter of 0.21-2.53 mm.

The granules were classified by a vibrating classifier to obtain 14.6 kg of granules having 0.355-0.850 mm size, and other granules out of said range were dried and disintegrated and recycled by being applied to the molding process again.

The granules having 0.355-0.850 mm size obtained from the classification process were dried in a fluidized bed at 90° C., then calcinated in a batch type rotary furnace (manufactured by Lindberg, US) at 350° C. and allowed to stand still under atmospheric conditions for a sufficient time, thereby resulting in a NaX type granules of 10.9 kg.

Thus obtained granules were placed into an aqueous solution in which sodium hydroxide 2.73 kg were dissolved in water 21.8 kg and aged at 35° C. for 12 hours. Then, the temperature of the total reactant was elevated to 90° C. to carry out a hydrothermal reaction thereof for 8 hours, and then the mother liquor for the reaction was removed and sufficiently washed.

To the hydrothermally-reacted granules, an aqueous solution of 2N $BaCl_2$ heated to 70° C. was contacted at the flow rate of 1.5 l/minute for ion exchange. The ion exchange was conducted until the ion exchange rate by $Ba^{2+}$ ions was reached to approximately 92%. The resulted product was sufficiently washed and dried in a fluidized bed type dryer at 105° C.

The ion exchanged granules were placed in a batch type rotary furnace (manufactured by Lindberg US) at 500° C., activated by sufficiently feeding water- and carbon dioxide-free air therein, and then placed into a sealed container while flowing the high purity nitrogen, thereby finally obtaining BaX type zeolite granules 8.6 kg.

Comparative Example

A NaX type zeolite powder (water content 5.40 wt %) 14.0 kg, a recycled zeolite powder 6.0 kg (average particle size: 32 μm; water content: 6.50 wt %), clay of montmorillonite family 0.53 kg and clay of kaolin family 2.05 kg were placed into a 130 l volume flowshear mixer (Germany), and mixed together at the spindle rotational speed of 180 rpm and the chopper rotational speed of 3600 rpm for 1 min.

Next, water 7.23 kg was consistently fed to the above prepared powder mixture via nozzle and kneaded together, and granulation was carried out for 15 minutes to obtain irregularly-shaped granule having a particle diameter of 0.1-5.86 mm.

The granules were classified by a vibrating classifier to obtain 11.7 kg of granule having a size ranged of 0.355-0.850 mm, and other granules out of said range were dried and disintegrated and recycled by being applied to the molding process again.

The granules having 0.355-0.855 mm size obtained from the classification process were dried in a fluidized bed at 105° C., then calcinated in a batch type rotary furnace (manufactured by Lindberg, US) at 680° C. and allowed to stand still under atmospheric conditions for a sufficient time, thereby resulting in a NaX type granules of 8.9 kg.

Thus obtained granules were placed into an aqueous solution in which sodium hydroxide 2.5 kg was dissolved in water 18.2 kg, and aged at ambient temperature for 12 hours. Then, the temperature of the total reactant was elevated to 90° C. to carry out a hydrothermal reaction thereof for 8 hours, and then the mother liquor for the reaction was removed and sufficiently washed.

Then, the next procedures same as in the above example were carried out to obtain 6.5 kg of BaX type zeolite granules.

Experimental Examples

With the samples prepared by the above example and comparative example, the following physical properties were tested. The results were represented in the following Table 1.

Para-Xylene Adsorption

A sample was degassed at about 350° C. for a sufficient period of time, then para-xylene adsorption was measured by plotting an isothermal line under the conditions of a constant temperature of 177° C. and a constant pressure of 8.9 kg.

Abrasion Resistance

The abrasion resistance of a sample was carried out by a hardness test of a granular material according to KS-M-1802 (JIS-K-1474). A sample and steel ball were placed and agitated together in a bowl for a hardness test, and then classified. The weight of samples remained on the upper part of the classifier was measured. The weight ratio thereof to the weight of the original sample was calculated and the resulted value is determined as hardness.

$$H=(W \div S) \times 100 \quad \text{[Equation 1]}$$

wherein H is abrasion resistance (hardness, %); W is the weight (g) of samples remained on the upper part of a sieve; and S is the total weight (g) of the samples remained on the standard sieve and the samples in a receiving container.

Bulk Density

The sample was placed in a 100 ml volume mass-flask and sufficiently tapped at a certain height. Next, the volume (V, ml) and the weight (W, g) were measured and calculated by the following equation.

$$\text{Bulk density}=W/V \quad \text{[Equation 2]}$$

Amount of Para-Xylene Generated

For the measurement of para-xylene separation capability of the sample, a SMB device comprised of 12 adsorption columns was used. Each column was filled with 425 g of the adsorbent prepared in the example or comparative example. To the device, a liquid composition comprising 27 wt % of para-xylene, 46 wt % of meta-xylene, 22 wt % of ortho-xylene and 5 wt % of ethylbenzene was fed to each column at the rate of 70 ml/min. by taking turn to each column in periodical way for selective adsorption para-xylene. Then, subsequently para-diethylbenzene was periodically fed to each column for desorption of the adsorbed para-xylene. The composition separated by desorption was distilled to obtain para-xylene with the purity of 99.71%, and the amount of obtained para-xylene was measured and calculated as an amount (g) per 1 g of the adsorbent and 1 hour.

TABLE 1

| | Para-xylene adsorption (g/g) | Abrasion resistance (%) | Bulk density (g/ml) | Amount of Para-xylene generated (g/g · hour) |
|---|---|---|---|---|
| Example | 0.098 | 98.9 | 0.69 | 0.109 |
| Comparative example | 0.082 | 93.1 | 0.63 | 0.091 |

As seen from the above Table 1, the BaX type zeolite granules prepared according to the present invention achieved excellent properties including para-xylene adsorption, abrasion resistance and para-xylene generation, superior to those properties of the comparative example which utilized a clay type inorganic binder.

INDUSTRIAL AVAILABILITY

The BaX type zeolite granule prepared by the method according to the present invention has pores uniformly well-formed even inside the granule, thereby having excellent adsorptive separation property, high bulk density, superior mechanical strength and being suitably used as an adsorbent in SMB process under high temperature and pressure conditions for para-xylene adsorptive separation.

The invention claimed is:

1. A method for preparing BaX type zeolite granules, comprising:
   (1) adding a carbohydrate-based molding promoter to NaX type zeolite powder, spraying alumina sol and silica sol thereto, and blending them together to form granules;
   (2) classifying the granules to obtain granules having a size of 0.25-1.20 mm;
   (3) drying the obtained granules and then calcinating the dried granules at the temperature range of 200-500° C. so as to remove the carbohydrate-based molding promoter, thereby generating pores;
   (4) placing the calcinated granules obtained from the step (3) in an aqueous solution of sodium hydroxide to allow a hydrothermal reaction, and separating and washing the resulted granules from the reaction solution;
   (5) treating the granules obtained from the step (4) with aqueous barium ion solution for ion-exchange, and then washing and drying the resultant; and
   (6) heating the dried granules obtained from the step (5) at the temperature range of 350-650° C. to remove water of crystallization from the granules, thereby activating the granules.

2. The method according to claim 1, wherein the carbohydrate-based molding promoter used in the step (1) is selected from cellulose, lignin, starch and alginic acid, and used at the amount of 5-25 parts by weight based on 100 parts by weight of the zeolite.

3. The method according to claim 1, wherein the amount of alumina sol used in the step (1) is 10-40 parts by weight based on 100 parts by weight of the zeolite, and the amount of silica sol used in the step (1) is 20-80 parts by weight based on 100 parts by weight of the zeolite.

4. The method according to claim 1, wherein the granules left out of the range of 0.25-1.20 mm from the step (2) are dried, disintegrated and powdered to be recycled to the step (1).

5. The method according to claim 4, wherein the amount of powder recycled to the step (1) is 20-50 wt % of the total amount of zeolite feed.

6. A BaX type granular zeolite prepared by the method according to any one of claims 1 to 5.

7. The BaX type granular zeolite according to claim 6, wherein the BaX type granular zeolite contains 90.0 wt % or more of zeolite, 10.0 wt % or less of aluminosilica on a solid basis.

8. The BaX type granular zeolite according to claim 7, wherein the granular zeolite has the ion exchange ratio by barium ion of 85% or more.

9. The BaX type granular zeolite according to claim 8, wherein the granular zeolite has 0.095 g/g or more of para-xylene adsorption capability, 97% or more of abrasion resistance, 0.65 g/ml or more of bulk density and 0.102 g/hour or more of para-xylene generation per 1 g of the BaX type granular zeolite, from a para-xylene producing device using a SMB process.

* * * * *